(12) United States Patent
Zaffagnini

(10) Patent No.: US 12,727,989 B2
(45) Date of Patent: Sep. 8, 2026

(54) DEVICE FOR SURGICAL RECONSTRUCTION OF A CRUCIATE LIGAMENT

(71) Applicant: Istituto Ortopedico Rizzoli, Bologna (IT)

(72) Inventor: Stefano Zaffagnini, Bologna (IT)

(73) Assignee: Istituto Ortopedico Rizzoli, Bologna (IT)

( * ) Notice: Subject to any disclaimer, the term of this patent is extended or adjusted under 35 U.S.C. 154(b) by 852 days.

(21) Appl. No.: 17/614,129

(22) PCT Filed: Apr. 27, 2020

(86) PCT No.: PCT/IB2020/053928
§ 371 (c)(1),
(2) Date: Nov. 24, 2021

(87) PCT Pub. No.: WO2020/240303
PCT Pub. Date: Dec. 3, 2020

(65) Prior Publication Data

US 2022/0218463 A1 Jul. 14, 2022

(30) Foreign Application Priority Data

May 30, 2019 (IT) ........................ 102019000007665

(51) Int. Cl.
*A61F 2/08* (2006.01)

(52) U.S. Cl.
CPC ..... *A61F 2/0811* (2013.01); *A61F 2002/0882* (2013.01); *A61F 2210/0004* (2013.01);
(Continued)

(58) Field of Classification Search
CPC ............ A61F 2/0811; A61F 2002/0882; A61F 2013/5672
See application file for complete search history.

(56) References Cited

U.S. PATENT DOCUMENTS 5,425,766 A * 6/1995 Bowald .................. A61L 27/58
623/13.18
2005/0090827 A1 4/2005 Gedebou
(Continued)

FOREIGN PATENT DOCUMENTS

WO 8404669 A1 12/1984
WO 8901320 A1 2/1989
(Continued)

OTHER PUBLICATIONS

International Search Report and Written Opinion dated Aug. 11, 2020. 13 pages.

*Primary Examiner* — Christopher D. Prone
(74) *Attorney, Agent, or Firm* — RMCK Law Group PLC

(57) ABSTRACT

Described herein is a device for an intervention of reconstruction of a cruciate ligament that includes a penetrator defining a first passage lumen, and a sleeve member coupled to the penetrator and defining a second passage lumen that is in communication with the first passage lumen. The penetrator is configured for being introduced into a tibial plate and for receiving a replacement cruciate ligament through the first passage lumen. The sleeve member is configured for receiving the replacement cruciate ligament through the second passage lumen.

9 Claims, 8 Drawing Sheets

(52) U.S. Cl.
CPC . *A61F 2220/0016* (2013.01); *A61F 2220/005* (2013.01); *A61F 2220/0058* (2013.01); *A61F 2220/0075* (2013.01); *A61F 2230/0006* (2013.01); *A61F 2230/0017* (2013.01); *A61F 2230/0065* (2013.01)

(56) References Cited

U.S. PATENT DOCUMENTS

2006/0041261 A1* 2/2006 Osypka .............. A61B 17/8685 606/328
2015/0127027 A1* 5/2015 Vandewalle .......... A61F 2/0811 606/151

FOREIGN PATENT DOCUMENTS

WO 2013142131 A1 9/2013
WO WO-2016164588 A1 * 10/2016 ............. A61B 17/04

* cited by examiner

DEVICE FOR SURGICAL RECONSTRUCTION OF A CRUCIATE LIGAMENT

CROSS-REFERENCE TO RELATED APPLICATIONS

This application is a 371 National Stage of International Application No. PCT/IB2020/053928, filed Apr. 27, 2020, which claims priority to Italian Patent Application No. 102019000007665 filed May 30, 2019. The disclosure of each of the above applications is incorporated herein by reference in its entirety.

FIELD OF THE INVENTION

The present invention relates to orthopaedic surgery, in particular to interventions of reconstruction of cruciate ligaments.

PRIOR ART AND GENERAL TECHNICAL PROBLEM

In the field of orthopaedic surgery of reconstruction of cruciate ligaments resort is in general made to surgical techniques that envisage implantation of a new ligament—as a replacement of the native one—and routing thereof in a channel obtained artificially via bone perforation of the tibia. In this way, the aim is to reproduce as far as possible the arrangement and functionality of the native ligament.

The new ligament is typically obtained by harvesting autologous tendons, for example the semitendinosus tendon, the gracilis tendon, or the patellar tendon, or else by harvesting tendon from a donor, including a cadaveric donor.

In the case considered by way of example of reconstruction of the anterior cruciate ligament, a channel is made which traverses the tibia and gives out onto the point of insertion of the native anterior cruciate ligament, and then the replacement ligament is fixed at one end to the tibia, is routed through the channel, and is finally fixed to the femur at the opposite end. Fixing of the ends of the replacement ligament may be obtained either by means of terminal bushing or ring elements that gird the end of the ligament acting as axial contrast element, or with metal stitches that penetrate into the bones and pinch a corresponding end of the replacement ligament, thus securing it.

One of the problems inherent in these surgical techniques is a reconstruction of the native ligament that is exclusively functional, i.e., a reconstruction that does not extend also to achieving accurate restoration of the anatomy. For example, mere routing of the replacement ligament in the channel obtained by perforation of the tibia does not in effect enable any reproduction of the anatomical insertion of the native ligament, moreover leaving the replacement ligament exposed to the interaction with the walls and ends of the channel, a condition that is considerably different from the natural one present at the insertion of the native ligament.

OBJECT OF THE INVENTION

The object of the present invention is to overcome the technical problems mentioned previously.

In particular, the object of the invention is to provide a device for a surgical intervention of reconstruction of a cruciate ligament that will make it possible to proceed also to an anatomical reconstruction of the ligament itself, in particular of the insertion of the native ligament.

SUMMARY OF THE INVENTION

The object of the present invention is achieved by a device having the features forming the subject of the appended claims, which form an integral part of the technical disclosure provided herein in relation to the invention.

BRIEF DESCRIPTION OF THE FIGURES

The invention will be now described with reference to the attached figures, provided purely by way of non-limiting example, and wherein:

Some of FIGS. 1 to 7 represent, for graphic reasons, some of the components in see-through view. The connection lines of the reference numbers indicate the position of the component with respect to the point of observation by means of their graphic coding (dashed line or solid line). FIGS. 8A-8E and 9A, 9B comprise, where appropriate, two views set side by side corresponding to a cross-sectional view and to the corresponding front view.

DETAILED DESCRIPTION

Figure 1:
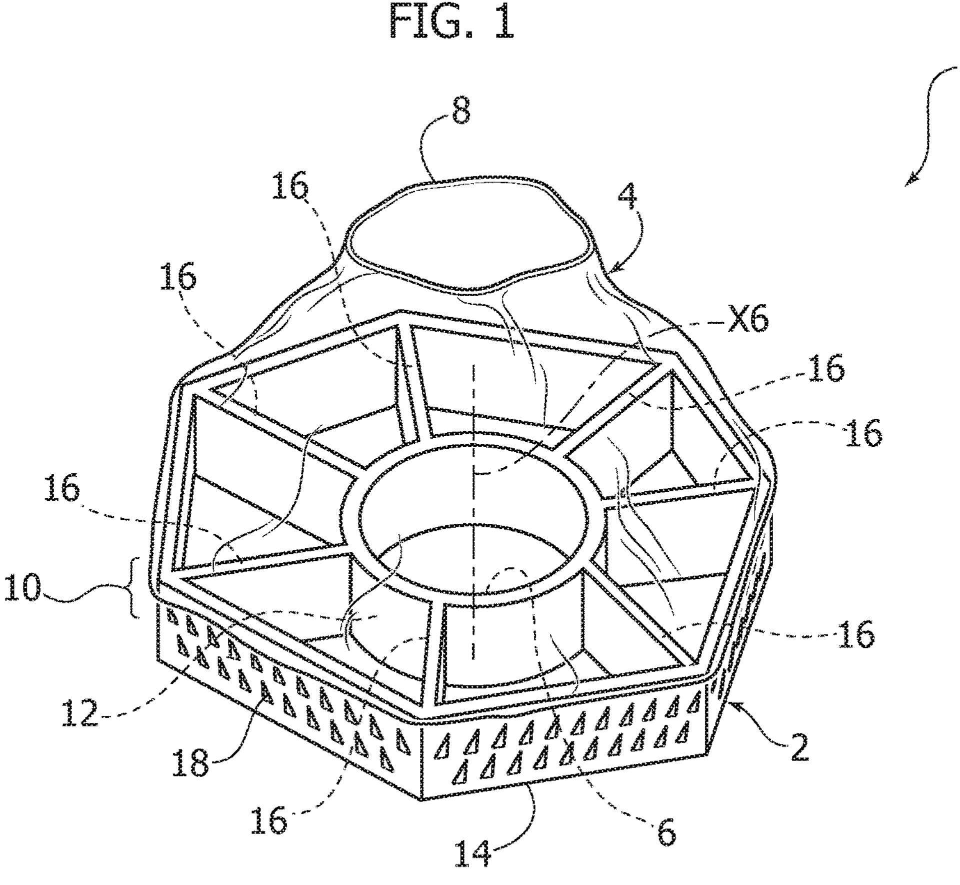
FIG. 1 is an overall perspective view of a device according to the invention.

The reference number 1 in the annexed figures designates as a whole a device for an intervention of reconstruction of a cruciate ligament according to the invention. The device 1 comprises a penetrator 2, and a sleeve member 4 coupled to the penetrator 2. The penetrator 2 defines a first passage lumen 6, whereas the sleeve member 4 defines a second passage lumen 8, where the second passage lumen 8 is in communication with the first passage lumen 6.

Figure 2:
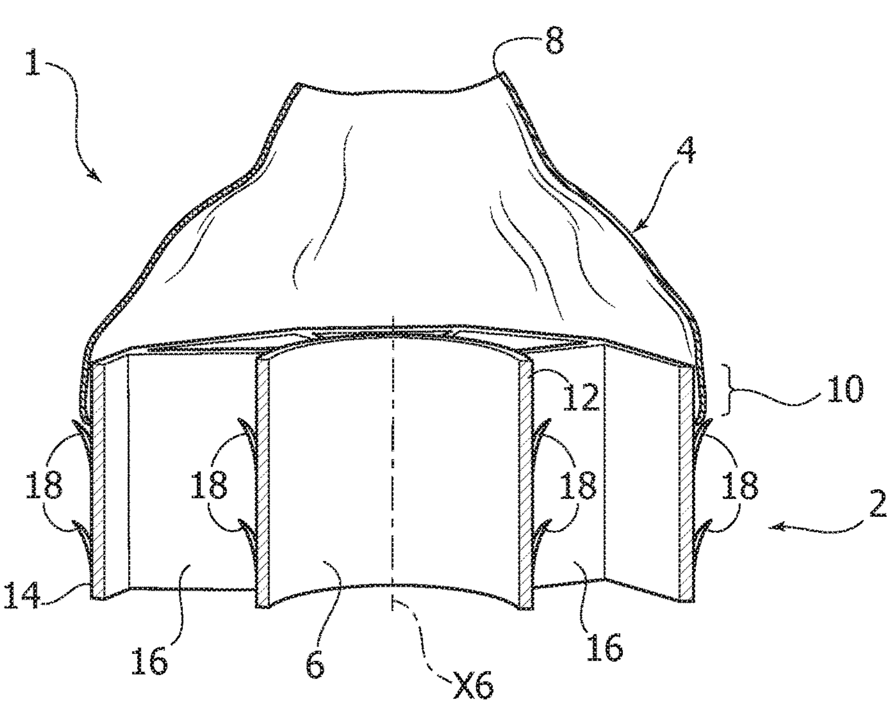
FIG. 2 is a longitudinal sectional view of the device of FIG. 1.

With reference to FIGS. 1 and 2, number 10 designates as a whole a coupling interface between the penetrator 2 and the sleeve member 4.

Figure 3:
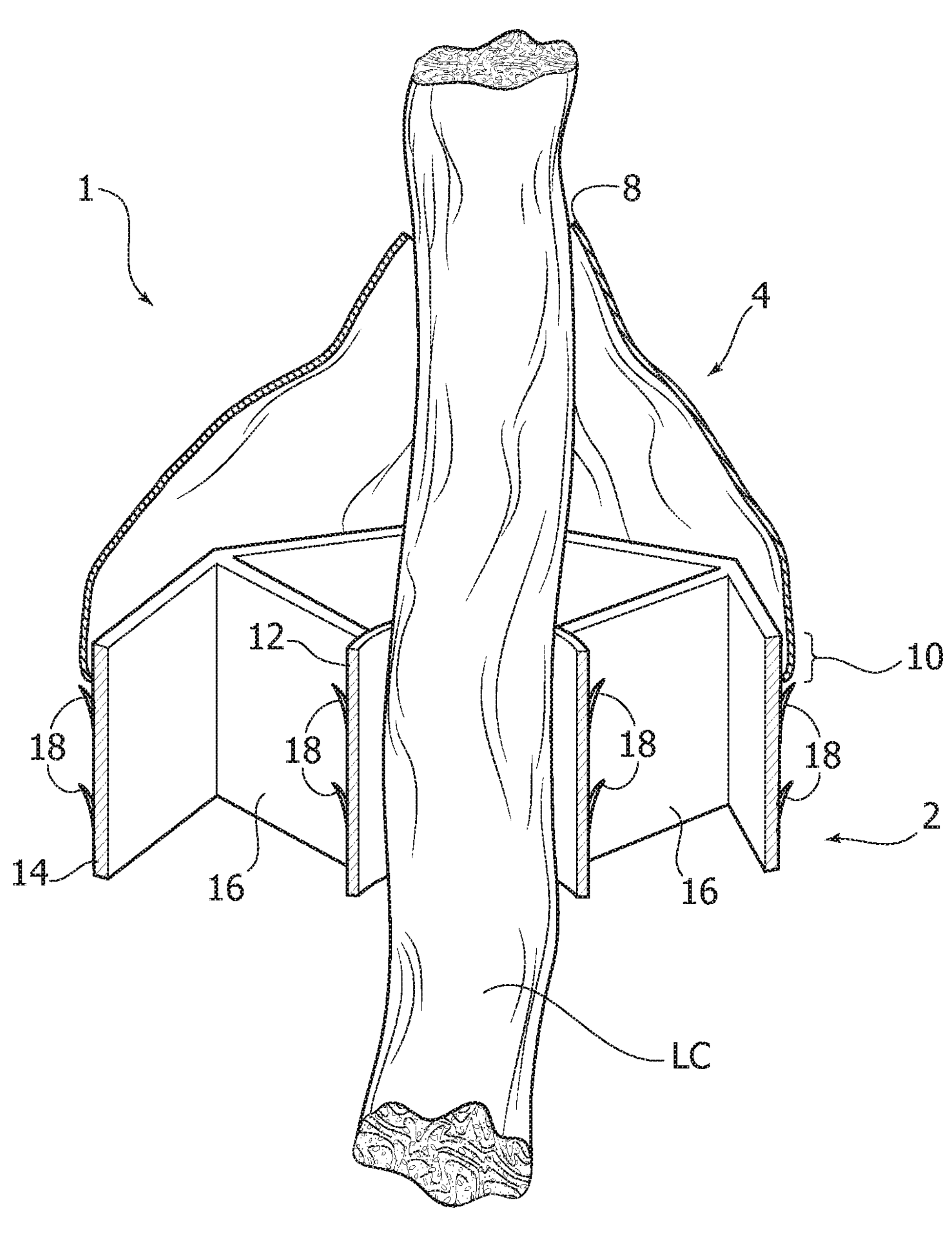
FIG. 3 corresponds to the sectional view of FIG. 2, but moreover represents routing of a (reconstruction) replacement ligament.

With reference to FIGS. 1 to 3, in a preferred embodiment, the penetrator 2 comprises a central annular member 12 defining the first passage lumen 6 (with corresponding axis X6), a peripheral annular member 14 surrounding the central annular member 12, and a plurality of spokes 16 extending in the radial direction with respect to the annular member 12 and connecting the latter to the member 14.

As regards the outer annular member 14, it may have a circular shape, or else preferably a polygonal shape, even more preferably an irregular polygonal shape.

Furthermore, while having the polygonal shape—preferably irregular as illustrated in the figures—, the penetrator 2 may present a constant thickness in an axial direction (axis X6), or else a thickness differentiated between the annular member 14 and the annular member 12, or else again a variable thickness—for the member 14 and/or for the member 12—proceeding around the axis X6.

With such a structure of the penetrator 2, the coupling interface 10 is provided on the outer surface of the peripheral annular member 14, and hence develops along a plurality of segments corresponding to the sides of the polygon that defines the annular member 14. The sleeve member 4 hence assumes the shape of a cuff having a first end edge coupled to the penetrator at the interface 10, and a second end edge that defines an outlet of the second passage lumen 8.

In various embodiments, the penetrator 2 may be made of a material chosen from among trabecular titanium, non-resorbable biocompatible materials, resorbable biocompatible materials, structured hydroxyapatite, bioglass, keratin, synthetic-bone material, composite materials comprising, for example, and polylactic acids or PEEKs mixed with one or more of the aforementioned materials so as to ensure mechanical properties compatible with penetration into the bone.

By way of example, in one embodiment, the penetrator 2 is made of a mixture of keratin-reinforced bioglasses. In another embodiment, the penetrator 2 may be made, alternatively, of:

PEEK and polylactic acid reinforced with hydroxyapatite or else with synthetic bone;

bioglass reinforced with synthetic bone; and

PEEK and polylactic acid reinforced with keratin.

As regards the sleeve member 4, it is a member made of a compliant material comprising, for example, bovine pericardium, connective tissue, hyaluronic acid, type-1/2 collagen, silk, or else a mixture of different materials, for example hyaluronic acid and collagen with a meshed structure.

According to the materials of which the penetrator 2 and the sleeve 4 are made, the connection interface 10 may be provided according to at least one of the following modalities:

i) a line of stitching;

ii) thermal or ultrasonic bonding;

iii) chemical bonding; and iv) gluing.

In case i) (line of stitching), the penetrator 2 is preferably made of trabecular titanium, whereas the sleeve 4 is made of bovine pericardium. The penetrator comprises a perimetral band that runs along the member 14 in correspondence of which a plurality of stitching holes are provided configured for receiving a stitching thread, which fixes the first end edge of the sleeve member 4 to the annular member 14.

In cases ii) and iii), the sleeve member 4 may be provided as a mesh of collagen or of a mixed composition of hyaluronic acid and collagen, whereas the penetrator 2 may be made of bioglass.

In this regard, as will emerge more clearly from the ensuing description, particularly advantageous are embodiments where the penetrator 2 is made of resorbable bioglass, whereas the sleeve member 4 is made as a collagen mesh. In this case, in addition to excellent chemical bonding between the bioglass and the collagen—which takes place through agglomerates of hydroxycarbonate apatite that are formed on the bioglass, generating a layer of gelatinous consistency at the interface—, biological integration with the implantation site and the replacement ligament proves optimal.

In case iv), the sleeve member 4 may again, by way of example, be provided as a collagen mesh and may be joined with a structural adhesive to a penetrator 2 made of inert bioglass.

Figure 8:
FIGS. 8A-8E sum up various embodiments of anchoring members of the device according to the invention.
Figure 8:
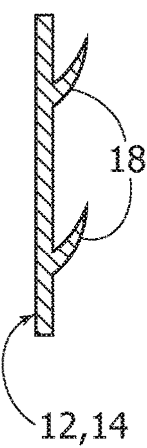
Figure 8:
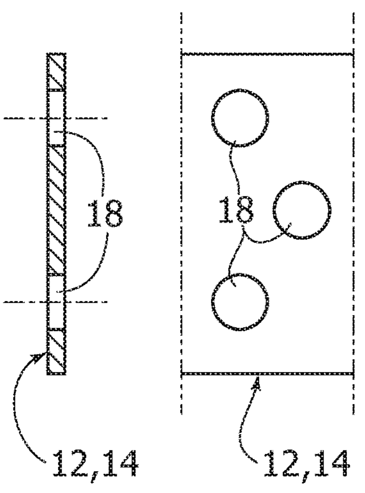
Figure 8:
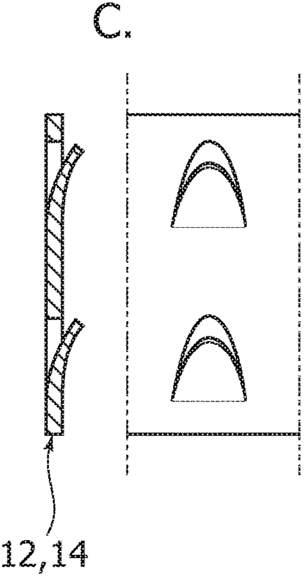
Figure 8:
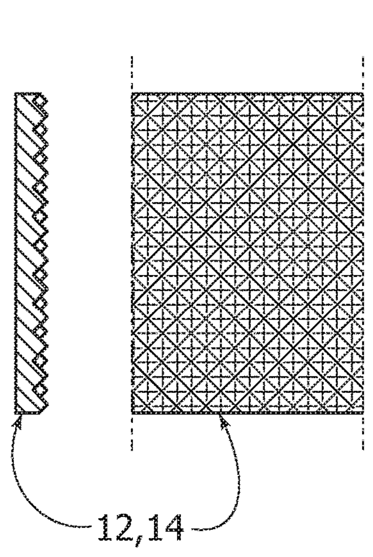
Figure 8:
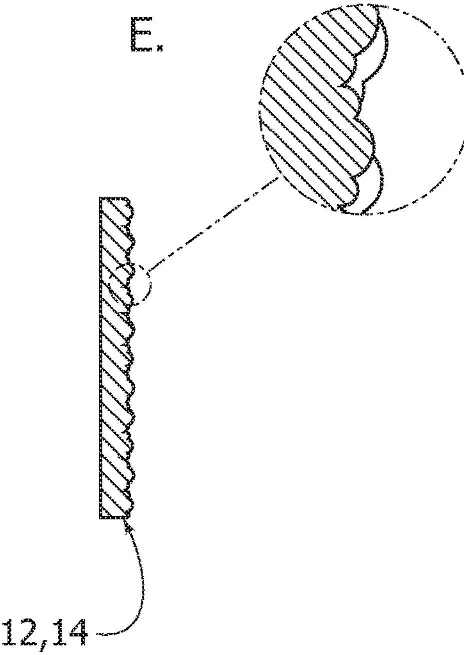

In addition, once again preferably, it is possible to provide on the outer surface of the peripheral annular member 14 and/or on the outer surface of the central annular member 12, the one facing the spokes 16, one or more anchoring members 18. With reference to FIGS. 8A-8E, the anchoring members 18 may comprise, individually or in combination, at least one of the following:

barbs (FIG. 8A);

through holes (FIG. 8B);

shearing of the wall of the penetrator 2 with radial protrusions (FIG. 8C);

a knurling (FIG. 8D); and a generic surface sculpturing, for example provided by increasing the roughness and/or by sand blasting or micro-bead blasting (FIG. 8E).

Operation of the device 1 and placement thereof will now be described.

Figure 4:
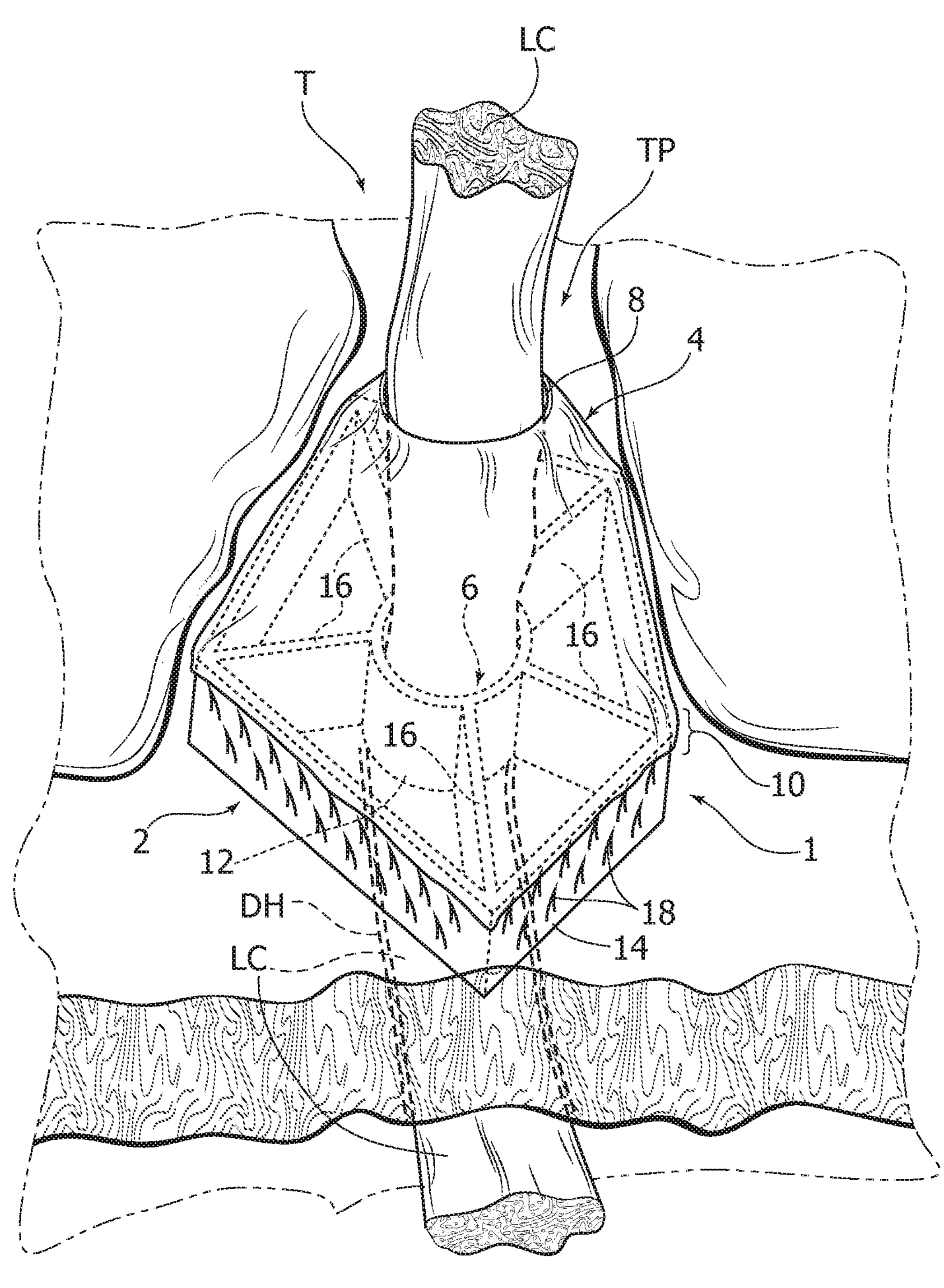
FIG. 4 illustrates a mode of placement of the device according to the invention.
Figure 6:
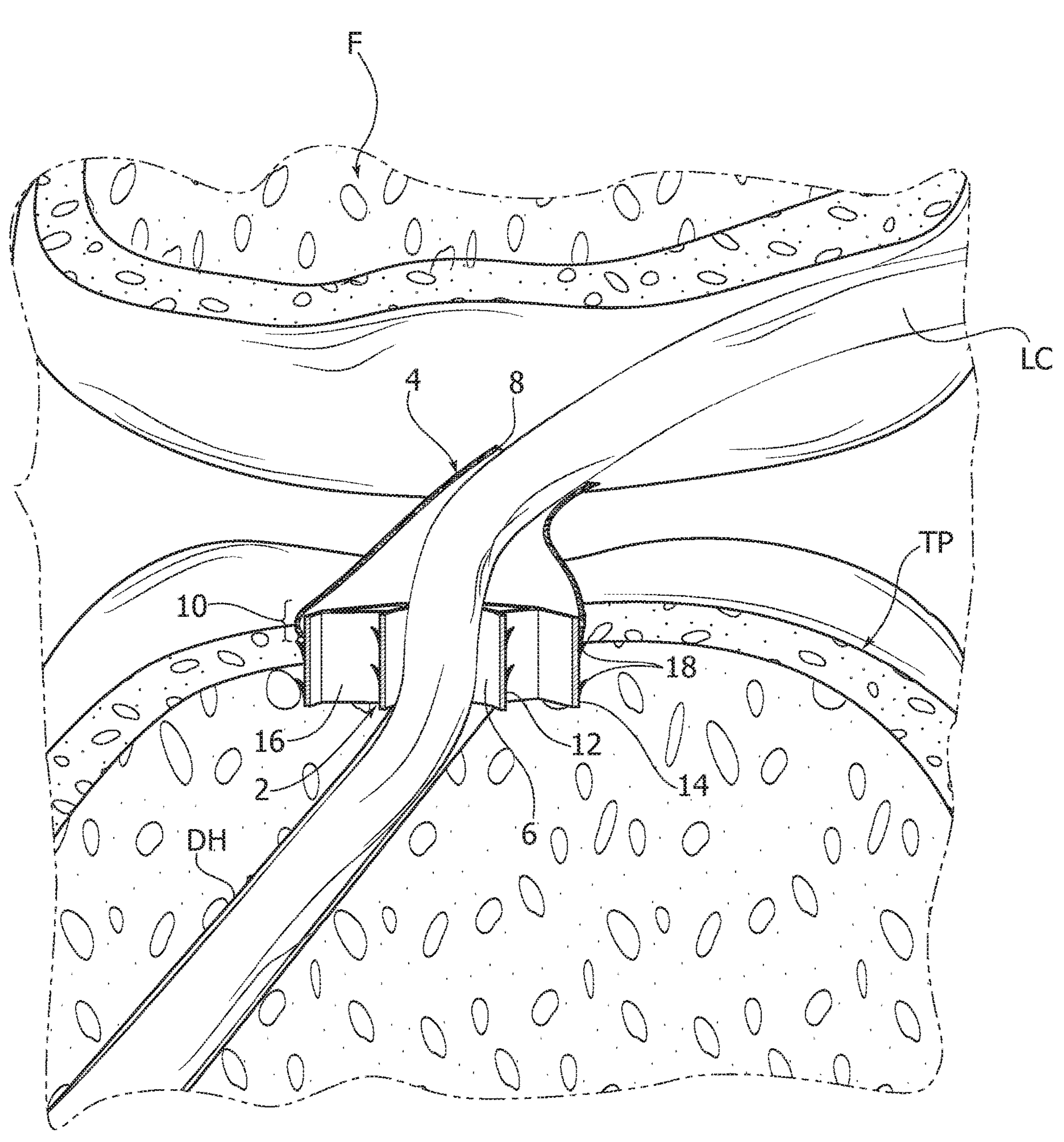
FIG. 6 is a detailed view according to the arrow VI of FIG. 5.
Figure 7:
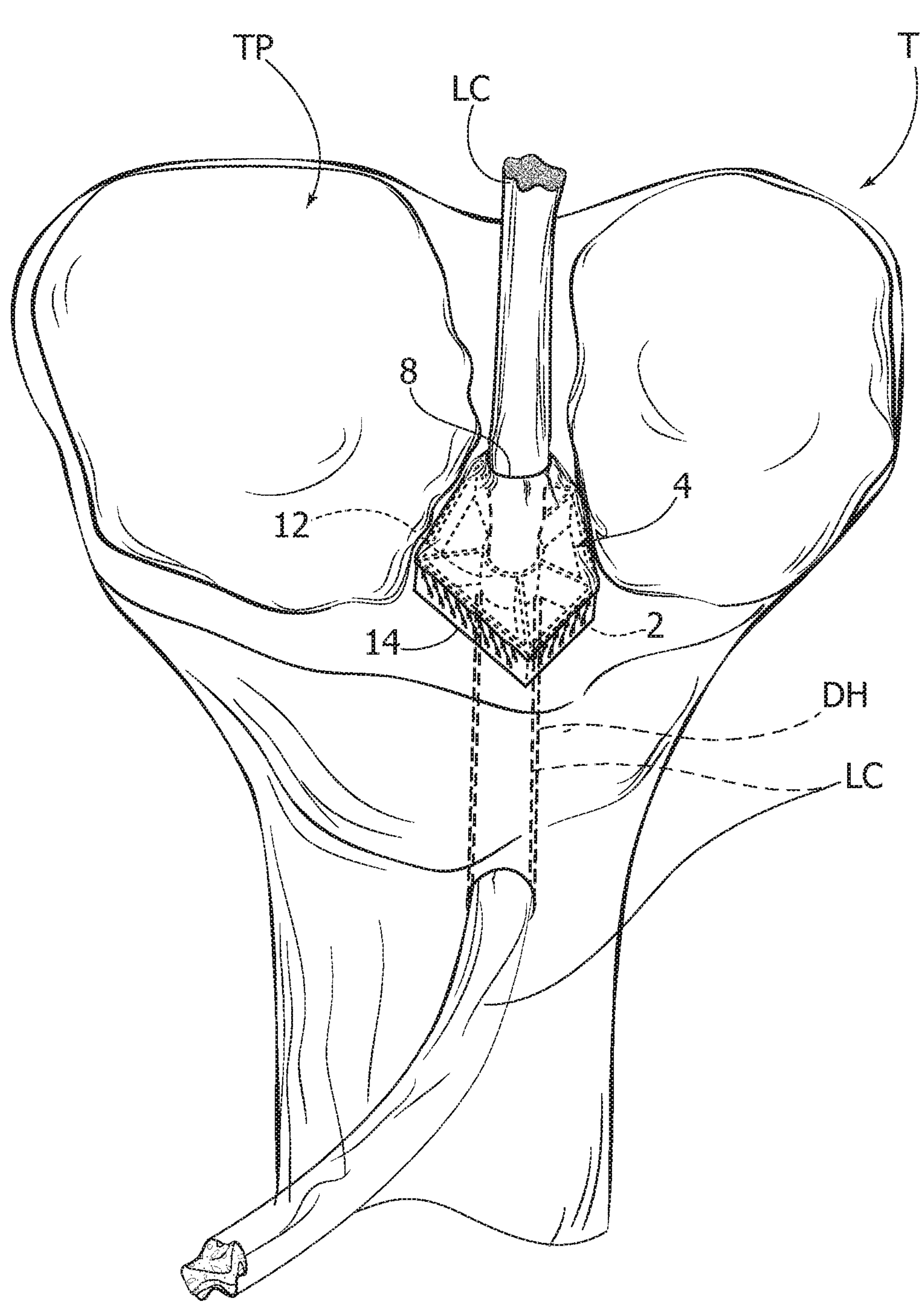
FIG. 7 is a perspective view of a tibial plate, which represents the device according to the invention set in place.

With reference to FIG. 4 and FIG. 6, the device 1 is configured for being introduced into the tibial plate TP of a tibia T. in particular, the penetrator 2 is shaped and sized in such a way that it can penetrate stably into the tibial plate in an intercondylar position basically corresponding to the natural insertion of the cruciate ligament.

Figure 9:
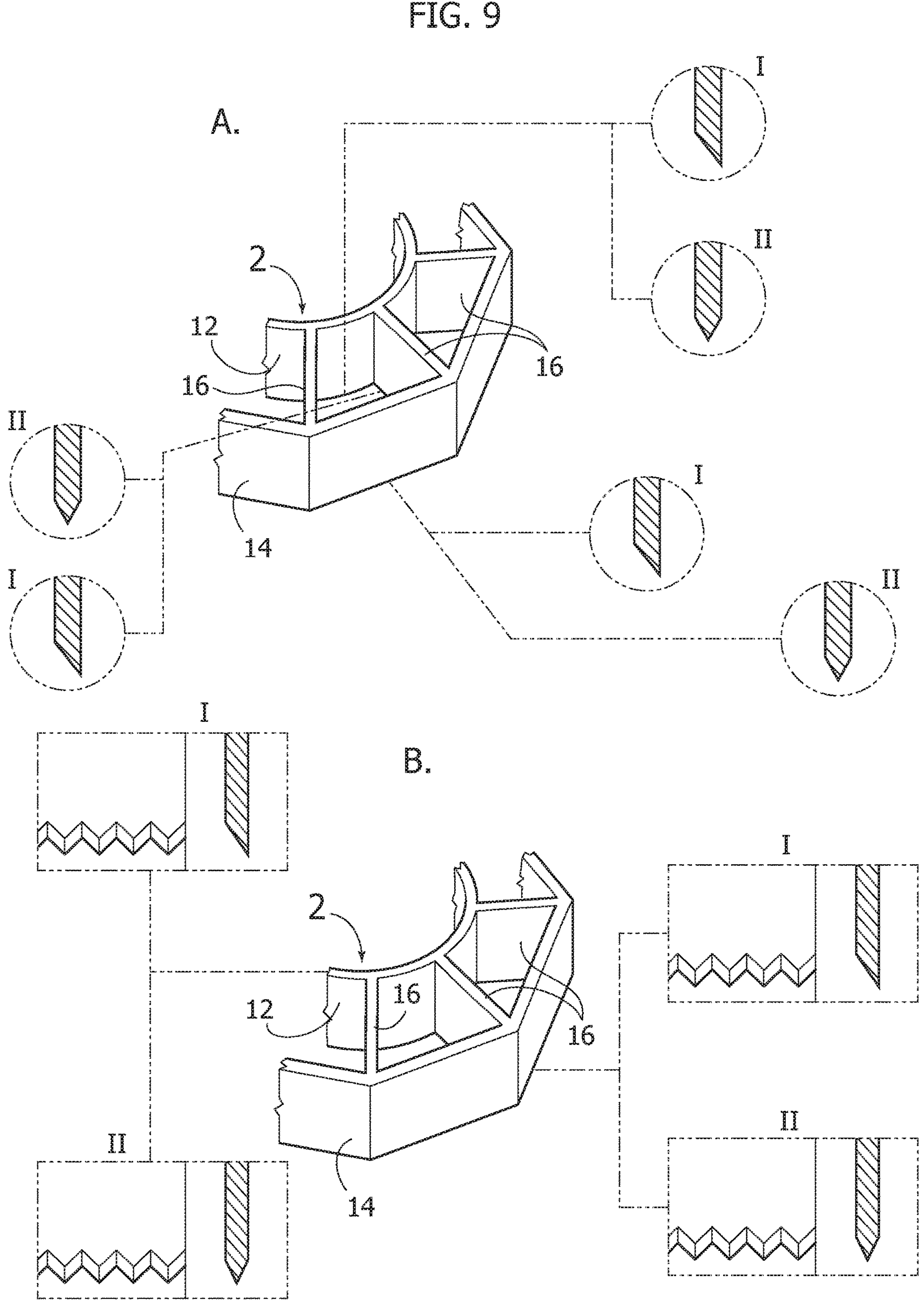
FIGS. 9A and 9B sum up various embodiments of a portion of a component of the device according to the invention.

For this purpose, with reference to FIGS. 9A and 9B, the ends of the penetrator 2 that are opposite to the coupling interface 10 and are configured for being the first to come into contact with the tibial plate TP may be shaped in such a way as to increase the capacity of penetration into the bone. For example, the bottom edge of the annular member 14, the bottom ends of the spokes 16, and the bottom circular rim of the annular member 12 may be wedge-shaped (FIG. 9A, alternative I) or arrow-shaped (FIG. 9A, alternative II) to increase their capacity of penetration into the bone, or else (FIG. 9B) may be provided with a serrated geometry, or again a serrated geometry with a combination of the two shapes described above (serration with wedge profile, FIG. 9B, alternative I, or else serration with arrow profile, FIG. 9B, alternative II).

Placement of the device 1 requires some preliminary operations, per se known, for preparation of the implantation site. In particular, positioning of the device 1 is preceded by the provision of a channel DH incident to the axis of the tibia T and giving out onto the tibial plate TP in a position substantially corresponding to the point of insertion of the native cruciate ligament. The position where the channel DH gives out onto the tibial plate TP in effect provides a position reference for the device 1, which is located on the tibial plate TP in such a way that the first passage lumen 6 is substantially made to coincide with the end of the channel DH that gives out onto the tibial plate TP. In this way, the first passage lumen 6 is in conditions such as to provide a local extension of the channel DH.

Once positioning of the device 1 has been carried out as described above, the surgeon can proceed with introduction thereof into the tibial plate TP, preferably by impulsive action such as a direct percussion (using a percussion tool) or an impact mechanism. In this latter case, the penetrator 2 can be coupled to an insertion tool that comprises a tie rod routed in the channel DH and fixed at one end to the penetrator 2. Fixed, instead, at the opposite end of the tie rod in question is a stop disk that functions as axial contrast element for an annular impact weight that can be slid along the tie rod. Upon insertion, the surgeon will simply have to drive the impact weight against the disk so that the constraint reaction on the disk will be transferred as far as the penetrator 2, thus driving the latter into the tibial plate TP.

Figure 5:
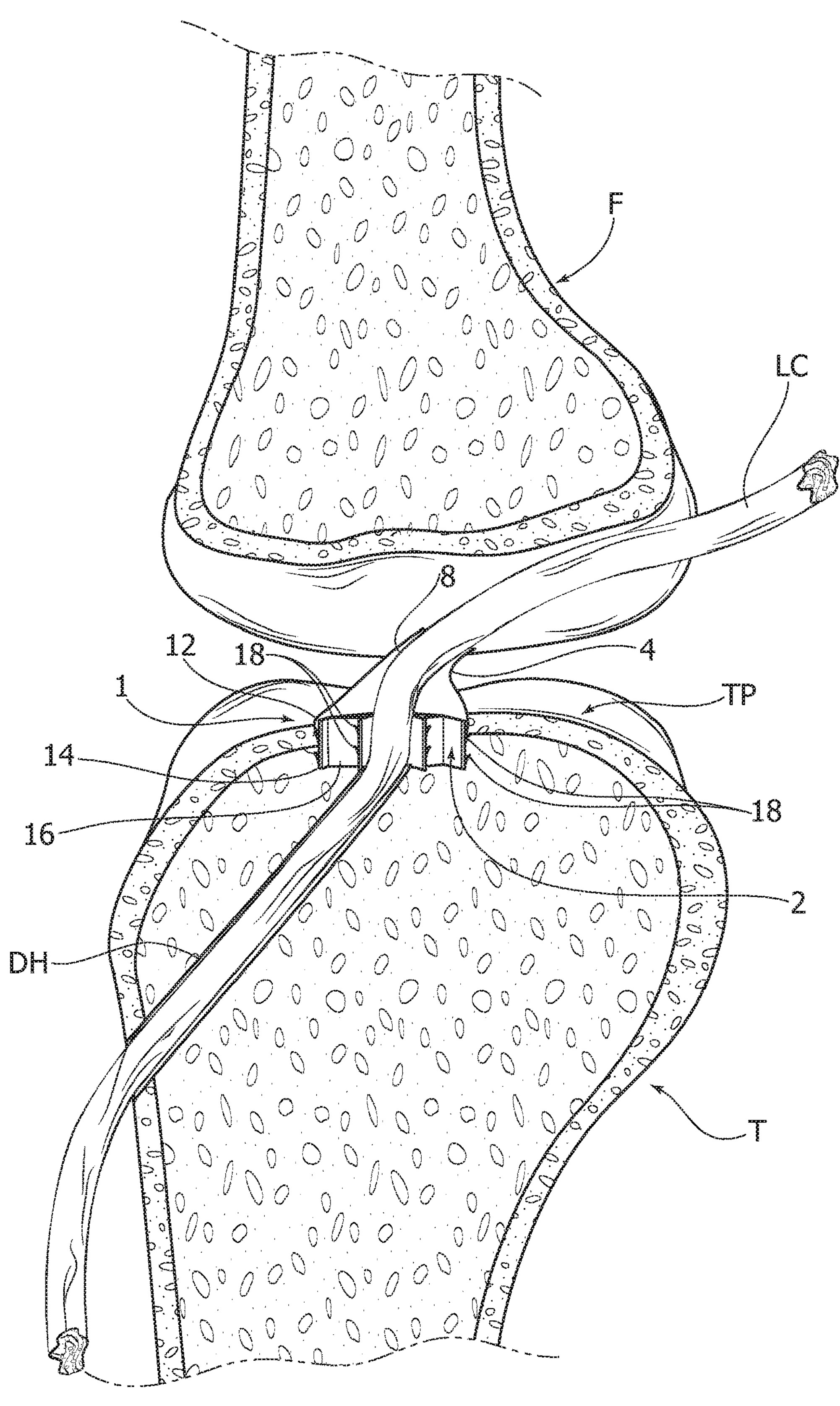
FIG. 5 is a complete cross-sectional view of the device according to the invention set in place.

With reference to FIG. 5, once introduction of the penetrator 2 into the tibial plate TP is completed, the penetrator is embedded within the tibial plate for a distance ranging between 3 mm and 5 mm. Once again with reference to FIG. 5, in this condition—thanks to the preliminary positioning of the device 1 with the aid of the channel DH—the first passage lumen 6 provides a prolongation of the channel DH so as to receive a replacement cruciate ligament LC. The latter, preferably following upon introduction of the penetrator 2 into the tibial plate TP, is fixed to the tibia T by means of any known surgical technique (metal braces or a terminal annular member), is routed in the channel DH, and at the outlet of the latter is then routed in the first passage lumen 6 and in the second passage lumen 8. As a whole, the replacement ligament LC traverses the device 1 entering from the side of the penetrator 2 (passage lumen 6) and coming out from the side of the sleeve member 4 (outlet of the passage lumen 8). The free end of the ligament LC that comes out of the sleeve member 4 can then be fixed to the femur F, once again with any known surgical technique, thus completing the operation of reconstruction of the ligament.

Use of the device 1 affords numerous benefits for the operation of reconstruction.

In the first place, in the weeks immediately subsequent to the intervention, the device 1 affords total protection for the replacement ligament LC thanks to the fact that the sleeve member 4 envelops the ligament LC—thus protecting it—in an area traditionally critical such as the one between the tibial plate TP and the femur F, where, as has been said, the ligament LC is to be supported not by a biological insertion, but by a mechanical block and is to be withheld by the walls of the channel DH.

In the second place, and this is even more important, both the penetrator 2 and the sleeve member 4 are made in such a way as to favour, respectively, bone regrowth and incorporation in the tibial plate (penetrator 2), and fusion with the replacement ligament LC (sleeve member 4). This means that, at a distance in time from the reconstructive intervention, there is in effect recreated a connection of the ligament LC to the tibial plate TP that presents characteristics altogether resembling the natural insertion of the native cruciate ligament. The penetrator 2 is indissolubly englobed in the tibia, and the sleeve member 4 forms a single piece with the penetrator 2 (and consequently the tibial plate TP) and the ligament LC.

Incorporation of the penetrator 2 within the tibial plate TP is on the other hand facilitated by the anchoring members 18 in the case where the penetrator 2 is not made of resorbable material (for example, hydroxyapatite, or any non-toxic and bioactive material). In this case, the provision of barbs and/or through holes enables a more convenient penetration of the new bone tissue, with creation of undercuts that permanently secure the penetrator 2 in the bone.

In the case where the penetrator 2 is made of resorbable material, incorporation would be even more developed. In this sense, as has been anticipated, particularly advantageous are embodiments where the penetrator 2 is made of resorbable bioglass, for example tricalcium phosphate, whereas the sleeve member is provided as a collagen mesh. In this case, in addition to the chemical bond between the penetrator 2 and the sleeve member, integration with the implantation site (tibial plate TP) and with the replacement ligament LC is total. In time, the penetrator 2, the material of which is non-toxic and resorbable, simply dissolves and is replaced by new bone tissue. The sleeve member 4, as described, fuses with the replacement ligament LC, but at this point it is directly interfaced with the new bone tissue that has replaced the dissolved penetrator 2, in effect reconstructing the natural insertion of the native cruciate ligament.

In all the embodiments, the penetrator 2 and/or the sleeve member 4 may be provided with differentiated or undifferentiated cells, which may comprise chondrocytes or fibrocytes or else stem cells. All these types of cells can in turn be produced in the laboratory in such a way as to build a tissue proper, and in this case they are defined as "expanded". It is, however, possible to use cells not produced in the laboratory ("not expanded"). Again, the penetrator 2 and/or the sleeve member 4 may be functionalized with, or associated to, proteins, growth factors, or other signal molecules or target molecules, such as to be able to favour further healing and adhesion of the sleeve member 4 to the replacement ligament LC that is introduced within it and at the same time favour the best possible integration of the penetrator 2 with the bone.

In summary, thanks to the device 1, there may be noted, at a distance in time from the reconstructive intervention, a fusion between the ligament LC and the tibial plate TP that operates in conditions, and is endowed with properties, that are practically identical to those of the native insertion.

Of course, the details of construction and the embodiments may be varied widely with respect to what has been described and illustrated herein, without thereby departing from the scope of the present invention, as defined by the annexed claims.

The invention claimed is:

1. A device for an intervention of reconstruction of a cruciate ligament, comprising:

a penetrator having an outer peripheral annular member and defining a first passage lumen, and a pliable cuff having a first end opening coupled to the peripheral annular member of the penetrator and an opposite second end opening spaced apart from the first end opening, the pliable cuff defining a pliable second passage lumen, the pliable second passage lumen being in communication with the first passage lumen, the second end opening being smaller than the first end opening and defining an outlet of said pliable second passage lumen, wherein:

the pliable cuff is generally tapered from the second end opening to the first end opening, the penetrator is constructed with a first material and the pliable cuff is constructed with a second material which is both pliable and different from the first material, the penetrator is configured for being introduced into a tibial plate and for receiving a replacement cruciate ligament through said first passage lumen, and the pliable cuff is configured for receiving the replacement cruciate ligament through said pliable second passage lumen.

2. The device according to claim 1, wherein said pliable cuff is made of resorbable material.

3. The device according to claim 1, wherein said penetrator comprises at least one anchoring member configured for securing the penetrator into the tibial plate following upon introduction thereof.

4. The device according to claim 3, wherein said at least one anchoring member comprises a set of barbs.

5. The device according to claim 3, wherein said at least one anchoring member comprises one or more apertures provided in said penetrator.

6. The device according to claim 1, wherein said penetrator comprises:

a central annular member;

the peripheral annular member surrounding said central annular member; and a plurality of spokes extending between and connecting said central annular member and said peripheral annular member.

7. The device according to claim 6, wherein said peripheral annular member has a polygonal geometry.

8. The device according to claim 7, wherein said polygonal geometry is irregular.

9. The device according to claim 1, wherein said pliable cuff is coupled to said peripheral annular member by means of one of the following:

stitching;

chemical bonding;

thermal or ultrasonic bonding; and gluing.

* * * * *